United States Patent [19]

Ackerman et al.

[11] Patent Number: 4,469,690

[45] Date of Patent: Sep. 4, 1984

[54] SYNERGISTIC COMPOSITIONS OF RENAL DOPAMINERGIC AGENT AND β-BLOCKER

[75] Inventors: Dennis M. Ackerman, Cherry Hill, N.J.; Barry A. Berkowitz, Fort Washington; Virgil D. Wiebelhaus, Springfield, both of Pa.

[73] Assignee: SmithKline Beckman Corporation, Philadelphia, Pa.

[21] Appl. No.: 442,051

[22] Filed: Nov. 16, 1982

[30] Foreign Application Priority Data

Dec. 8, 1981 [EP] European Pat. Off. ........ 81110252.4

[51] Int. Cl.³ .............................................. A61K 31/33
[52] U.S. Cl. .................................................... 424/244
[58] Field of Search ......................................... 424/244

[56] References Cited

U.S. PATENT DOCUMENTS 4,011,319  3/1977  Kaiser et al. ........................ 424/244
4,265,889  5/1981  Brush et al. .......................... 424/244
4,340,595  7/1982  Franke et al. ........................ 424/244

FOREIGN PATENT DOCUMENTS 22330  12/1983  European Pat. Off. .

OTHER PUBLICATIONS

Owen Pharmacy International, 1981, 17–21.

*Primary Examiner*—Jane T. Fan
*Attorney, Agent, or Firm*—William H. Edgerton; Richard D. Foggio; Alan D. Lourie

[57] ABSTRACT

Compositions useful for improving kidney function and treating hypertension are comprised of a 6-chloro, 6-fluoro or 6-methyl-7,8-dihydroxy-1-(4-hydroxyphenyl)-2,3,4,5-tetrahydro-1H-3-benzazepine combined with a β-adrenergic blocking agent known to the art, especially, propranolol. The compositions are administered, most readily, orally.

8 Claims, No Drawings

SYNERGISTIC COMPOSITIONS OF RENAL DOPAMINERGIC AGENT AND β-BLOCKER

This invention comprises a composition containing one of certain selected benzazepine compounds which have specific renal vasodilating activity after oral or parenteral administration but which do not, by themselves, elevate glomerular filtration, that is, a renal dopamine-like agent with a $D_1$ mechanism of action, combined with one or more known compounds which have β-adrenergic blocking activity. The composition which contains this new combination of medicinal agents demonstrates an improved efficiency of kidney function and an improved antihypertensive effect. An unexpected increase in the glomerular filtration rate, together with an inhibition of renin release, has been demonstrated with the combination product of this invention. Improved kidney function is beneficial to hypertensive patients but this result can also be useful in patients who may not be hypertensive, especially elderly patients or others with diminished renal function.

Renin is an enzyme which plays a major role in the release of the vasoconstricting compound, angiotensin II. The dopamine-like benzazepine ingredients of this invention have been found to increase the release of renin, presumably by the kidney. Adding the prototypal β-blocking agent, propranolol, to the selected benzazepine has been found to lower the level of renin in the circulatory system which has been observed following the administration of the benzazepine alone.

BACKGROUND OF THE INVENTION

The renal dopamine-like ingredients in the claimed compositions are described in U.S. Pat. Nos. 4,197,297 or 4,265,889. The β-blocking agents are old in the art and are described here by their accepted generic names. H. J. Sanders, Chemical and Engineering News, July 12, 1982 page 26 described the development, mechanism of action and utility of β-blocking agents. No prior art mention of the claimed compositions is known to the applicants.

Each of the components of the composition of this invention has been described in the literature to be useful combined with diuretics, for example see European patent application No. 22,330 published Jan. 14, 1981 and R. T. Owen, Pharmacy International 1981, 17–21. EP No. 22,330 describes the specifically acting renal dopaminergic agents of Formula I to have a synergistic natriuretic effect with thiazide diuretics but not with diuretics acting at sites other than the distal convoluted tubules. No increase in renal filtration rate was reported.

The Owen article discloses that β-blockers combined with diuretics are a useful combination in treating various cardiovascular conditions but that synergism cannot be demonstrated reproducibly.

DESCRIPTION OF THE INVENTION

The renal vasodilator component of this combination will be a compound of the structure:

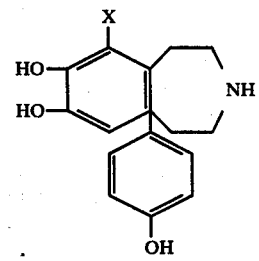

in which X is chloro, fluoro or methyl.

Also included are derivatives of these compounds which may either give rise to the parent compounds in vivo or be useful themselves, such as the nontoxic, pharmaceutically acceptable acid addition salts, for example, hydrochloride, hydrobromide, sulfate, phosphate, sulfamate, methyl sulfonate, maleate or fumarate salts. Prodrug derivatives include O-esters especially the tri-O-lower alkanoyl ester having from 2–8 carbon atoms in each alkanoyl group; O-methyl ethers or sulfate esters. The separated R and S stereoisomers are also useful.

The amounts of the compounds of Formula I present in the antihypertensive compositions are calculated on the base form although the acid addition salts are most conveniently used, especially, the hydrochloride, hydrobromide or methyl sulfonate. The prodrug, isomeric or salt forms are prepared by methods well known to the art.

The 3-benzazepine compounds of Formula I are described in the prior literature to have an antihypertensive effect in subjects having, or prone to have, elevated blood pressure. The compounds are presumed to work by means of a specific drug action at the peripheral dopaminergic receptors, especially in the kidney, thereby, increasing renal blood flow and decreasing renal vascular resistance. The quantity of the renal dopaminergic agent in the compositions of this invention will vary with the potency of its biological activity as well as with its pharmacodynamic characteristics. Such quantity is chosen from the dose ranges of the renal dopaminergic agent in the literature useful for treating patients alone or combined with a diuretic agent. Generally, the quantity of renal dopaminergic agent in a dosage unit of this invention will be selected from the range of about 15–500 mg. Using, for example, 6-chloro-7,8-dihydroxy-1-(4-hydroxyphenyl)-2,3,4,5-tetrahydro-1H-3-benzazepine, as the methyl sulfonate salt, from about 25–300 mg of base equivalent is used in the composition. Preferably, the quantity of renal agent will be chosen from the range of 50–150 mg. The resulting composition is administered from 1–6 times a day. Other renal dopaminergic agents may be used, basing their unit dosages on this daily regimen with consideration of their quantitative efficacy compared with the given compound.

In the standard test procedure for determining renal dopamine-like activity which uses infusion of the test compound in anesthetized normotensive dogs, the preferred and standard species, 6-chloro-7,8-dihydroxy-1-(4-hydroxyphenyl)-2,3,4,5-tetrahydro-1H-3benzazepine, as the methylsulfonic acid salt, has an $ED_{15}$ for lowering renal vascular resistance of 0.3 μg/kg. The details of this test procedure are presented in the literature references mentioned above. The tri-O-acetyl derivative of the preferred compound has an $ED_{15}$ of 25 μg/kg, the tri-O-isobutyryl derivative, 16 μg/kg. Referring to Formula I, the compound in which X is $CH_3$ has an $RVR-ED_{15}$ of 2.8 μg/kg; the compound in which X is F has an $RVR-ED_{15}$ of 0.83 μg/kg; the compound in which X is Cl as the R-isomer has an $RVR-ED_{15}$ of 0.31 μg/kg and as the S-isomer has an $RVR-ED_{15}$ of 0.94 μg/kg. The 3-benzazepine species which have renal dopaminergic activity, as those of Formula I, may be used by comparing their activity in the anesthetized dog protocol with that of the named standard species in preparing antihypertensively effective and nontoxic dosage regimens.

The renal vascular resistance $ED_{15}$ values in the infused anesthetized dog given above are useful to assess quantitative and qualitative biological properties of the 6-substituted 7,8-dihydroxy-1-(4-hydroxyphenyl-2,3,4,5-tetrahydro-1H-3-benzazepine compounds of Formula I. These compounds are most useful following oral administration. They are rapidly absorbed from the gastrointestinal tract. Therefore, the renal dopaminergic agent must be matched with conventional dosage regimens of the β-blocking agents considering the pharmacokinetic properties of each active component. This is accomplished by combining the renal dopaminergic agent with a β-blocker in standard dosage unit forms for administration from 1-6 times daily. Oral administration is preferred, but the two basic compounds of these new compositions are, also, useful as parenteral products.

Alternatively, the renal dopaminergic agent may be incorporated into a timed release dosage unit form in which several doses are treated for delayed or sustained release of the medicament. Such dosage units may comprise sustained release granules, sugar centered spheres or multilayered tablets in each of which the availability of the active ingredient is controlled by coating with a lipid or polymeric material. In such compositions, the β-blocking component would usually be present in immediately available form.

The β-blocking component of the antihypertensive compositions of this invention will be any such standard agent known to the art which will be present in the composition in quantities within its normal dosage unit and daily regimen ranges as detailed in the medical literature. Propranolol or one of its pharmaceutically acceptable acid addition salts, especially propranolol hydrochloride, is the preferred β-blocker component of this new combination product. Normally, the β-blocker will be selected to give a daily quantity selected from the range of about 1 mg to 400 mg, depending on its known potency. A particularly effective, nontoxic quantity of the β-blocking compound in a dosage unit will be chosen from about 5-300 mg, preferably 5-80.

Such known β-adrenergic blocking agents by their generic names, their dosage unit quantities and daily dose ranges are:

| β-blocking agent | Unit form | Unit dose (mg) |
|---|---|---|
| propranolol | tablets | 10-80 |
|  | ampule | 1-3 |
| alprenolol | tablets | 50 |
|  | ampule | 1 |
| atenolol | tablets | 50-100 |
| bemetizide | tablets | 10 |
| bupranolol | tablets | 40-100 |
| bunitrolol | tablets | 10 |
| butidrin | tablets | 50 |
| metoprolol | tablets | 50-100 |
| nifenalol | tablets | 50 |
| oxprenolol | tablets | 20-80 |
|  | ampule | 2 |

| β-blocking agent | Unit form | Unit dose (mg) |
|---|---|---|
| pindolol | tablets | 5-15 |
| sotatol | tablets | 160-640 |
| timolol | tablets | 5-15 |
| toliprolol | tablets | 10-50 |

Other compounds which have β-adrenoceptor blocking activity at a minimum as a part of their pharmacodynamic spectrum are practolol, prizidilol, acebutolol, labetalol, mepinalol, bunalol, nadolol or bufetalol. In fact any compound whose chemical structure contains the "β-blocking fragment",

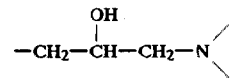

usually C-attached to an aromatic nucleus and, also, having a N-isopropyl or tert.-butyl substituent) and whose pharmacological activity includes a β-adrenergic blocking component can be used by comparing its relative potency as a β-blocker to that of the preferred propranolol.

We have, now, found that the administration to a subject, in need of an antihypertensive effect or of improvement in kidney function, of a specifically acting renal dopaminergic agent combined with a β-adrenergic blocking agent, each administered in accepted clinically effective quantities, unexpectedly increases the glomerular filtration rate (GFR) of the designated subject beyond that of simply adding the effects of the components. This unexpected biological effect, which was not previously reported in the renal dopaminergic-diuretic combination study contained in the European patent application mentioned above, is important in (1) increasing the sodium load presented to the tubules and (2) increasing the materials eliminated from the body by filtration such as metabolic waste products, especially, those of a nitrogenous nature such as urea. The compositions of this invention are, therefore, useful, for example, in improving kidney function of the elderly patient without increasing blood pressure or, even more so, in treating the hypertensive patient.

In addition to GFR synergism, the combination increases renal blood flow, natriuresis and balances plasma renin levels. The beneficial effect of the β-blocking agent on the increased renin plasma effect of the dopaminergic agent is unexpected. The β-blockers, especially propranolol, have been described in the prior literature to inhibit renin output by the kidney, only under certain circumstances, or to decrease renal blood flow. They are better known to decrease cardiac output and diminish tonic sympathetic nerve outflow from the vasomotor centers of the brain.

As stated above, the active renal dopamine-like and β-adrenoceptor blocking ingredients of the new compositions are not used in any critical ratio but each is used at one of its clinically effective doses. The resulting compositions exhibit the full spectrum of the biological activity of each of the ingredients with the unexpected synergistic effects discussed above and demonstrated hereafter.

The dosage unit compositions of this invention are prepared by standard pharmaceutical techniques by incorporation into a pharmaceutical carrier in the form of a dosage unit such as a tablet, troche, capsule or powder for either suspension or solution. For example, an effective quantity of a renal dopaminergic compound of Formula I selected from the dose ranges presented above together with an effective quantity of β-blocking agent selected from the dose ranges presented above are screened, sized and mixed together with a filler if need be, for example, talc, lactose, terra alba, magnesium stearate, agar, pectin, acacia, gelatin or stearic acid. The active ingredients and filler are mixed and filled into a hard gelatin capsule. Alternatively, the ingredients are tabletted using lubricants and granulating agents. Also, liquid carriers can be used, for example, peanut oil, sesame oil, olive oil or water. Such mixtures are encapsulated into soft gelatin capsules or, in case of a sterile, isotonic solution for parenteral use, in a unit or multidose vial.

If the renal dopaminergic agent is desired to be in a time release formulation, coating agents may be glyceryl distearate, wax, polyvinylpyrrolidone, zein, ethylcellulose, castor wax, polymethacrylates, cellulose acetate butyrate, a cross-linked polymeric film, for example, one formed from prepolymers of an unsaturated dicarboxylic acid and an ethylene compound, or acid copolymers formed from acrylic or methacrylic acid monomers.

The dosage unit compositions are administered orally to patients who have subnormal kidney function, abnormally high blood pressure or who are prone to have high blood pressure, usually, from 1-6 times daily preferably from 2-4 times daily. In certain cardiovascular emergencies, the combined compounds in pharmaceutically acceptable salt form may be dissolved or suspended in saline and administered parenterally. It will be appreciated tht the antihypertensive compositions of this invention combine clinically acceptable doses of a renal dopaminergic agent and a β-blocking agent with consideration for the half-life and peak therapeutic effect of each. It may be desirable in certain patients for the primary care physician to administer the two agents individually to achieve the novel therapeutic effect described herein. Also, under certain circumstances, a third agent from the same or another class of compounds may be added such as an oral dosage unit containing clinically effective quantities of 6-chloro-1-(4-hydroxyphenyl)-7,8-dihydroxy-2,3,4,5-tetrahydro-1H-3-benzazepine methyl sulfonate and propranolol hydrochloride with either hydrochlorothiazide or triamterene.

As treatment for short term cardiovascular emergencies, parenteral, usually intravenous, preparations are used for example containing doses selected from 1-3 mg/kg of propranolol and from 0.1-10 mg/kg of the preferred 6-chloro-1-(4-hydroxyphenyl)-7,8-dihydroxy-2,3,4,5-tetrahydro-1H-3-benzazepine methylsulfonic acid salt.

A modification of the phosphate-mannitol protocol, described in the prior art, was used for renal clearance studies in adult, trained, unanesthetized, fasted, female mongrel dogs, lightly restrained on their backs on a cradle-like board constructed specifically for this purpose. The effect of compound upon kidney function was determined by measurement of effective renal plasma flow (RPF), glomerular filtration rate (GFR), and filtration fraction (FF). Urine volume, pH and electrolyte excretion were also determined. The clearance of free water was calculated from plasma and urinary osmolalities.

All dogs were given an oral water load of 500 ml of tap water thirty minutes prior to initiation of the study. Using a constant infusion pump, the dogs were infused intravenously at 3 ml/minute throughout the course of the experiment with a 4% mannitol-phosphate buffer solution, pH 7.4. Glomerular filtration rate was determined by the clearance of creatinine and effective renal plasma flow by the clearance of p-aminohippuric acid (PAH). These clearances were determined simultaneously by including 0.4% creatinine and 0.08% p-aminohippuric acid in the infusion solution. Suitable plasma levels of creatinine and p-aminohippuric acid were obtained by a thirty minute infusion of this solution to obtain equilibrium prior to starting of the initial urine collection ($U_1$). In addition, 1.5 ml/kg of a 1% creatinine solution in phosphate buffer was injected intravenously fifteen minutes prior to collection of $U_1$. Replicate urine collections were obtained at ten minute intervals throughout the experiment. The bladder was emptied by an indwelling catheter and complete urine collections were assured by rinsing the bladder with 10 mls of warm water at the end of each collection interval. This procedure was followed by an air washout. Venous blood samples were drawn from an indwelling catheter at the mid-point of each clearance period.

Plasma and urine osmolalities were determined by freezing point depression on freshly obtained samples. Urine volume and pH were recorded at the time of collection. Plasma and urine samples were stored frozen, after collection, until analyzed. Analyses for sodium and potassium were made by flame photometry and for chloride, creatinine and p-aminohippuric acid, by colorimetry, using standard AutoAnalyzer methodologies. These analyses were made simultaneously on each sample. Peak intensities were identified electronically, recorded on "on-line" teletype, stored and subsequently analyzed mathematically by time-shared computer against appropriate standards. Data were computed from linear least square regression lines, and quality control standards were analyzed simultaneously to evaluate system reproducibility and reliability.

The bladder was emptied upon beginning the study and three control clearances ($U_1$–$U_3$, Phase 1) were obtained.

6-Chloro-7,8-dihydroxy-1-(4-hydroxyphenyl)-2,3,4,5-tetrahydro-1H-3-benzazepine as the methyl sulfonate salt was given orally by stomach tube at a dose 10 mg/kg of the base after Phase 1.

Propranolol hydrochloride was given in 4 ml of saline intravenously in order to obtain sufficient levels to insure biological activity during the period of the test after the 3rd clearance (Phase 1) at doses of 20 μg/kg, 0.5 mg/kg and 1.0 mg/kg.

Post-drug clearance $C_4$–$C_6$, $C_7$–$C_9$, $C_{10}$–$C_{12}$ (Phases II, III and IV) were collected immediately, with no delay between $C_3$ and $C_4$. The total post-drug period observed was one and one-half hours. Four dogs were used for each treatment.

All compounds were weighed as free base content.

Following are the results of testing the combinations using this protocol:

TABLE I

Comparison of the renal activity of a combination of propranolol hydrochloride and 6-chloro-7,8-dihydroxy-1-(4-hydroxyphenyl)-2,3,4,5-tetrahydro-1H-3-benzazepine methyl sulfonate (SK&F 82526-J) with that of each component in the mannitol-phosphate treated dog:

| Treatment | Control Phase I Clearances 1-3 Mean | Phase II Clearances 4-6 | Phase III Clearances 7-9 | Phase IV Clearances 10-12 |
|---|---|---|---|---|
| | | % Changes Post Drug RPF (ml/min) | | |
| A. SK & F 82526-J 10 mg/kg p.o. | 165.41 | 11.69 | 24.36* | 27.58* |
| B. Propranolol hydrochloride 0.5 mg/kg i.v. | 162.48 | −1.11<sup>f</sup> | −7.11<sup>f</sup> | −10.67<sup>f</sup> |
| C. Combination | 158.60 | 20.73* | 37.00* | 31.15* |
| | | | GFR (ml/min) | |
| A. SK & F 82526-J 10 mg/kg p.o. | 52.82 | −3.70 | −0.04 | −0.45* |
| B. Propranolol hydrochloride 0.5 mg/kg i.v. | 51.70 | 1.64 | −2.75 | −3.93<sup>f</sup> |
| C. Combination | 50.76 | 8.69* | 8.76* | 18.58* |
| | | | renin (ng/ml/min) | |
| A. SK & F 82526-J 10 mg/kg p.o. | 3.49 | 93.9<sup>f</sup> | 137.7<sup>f</sup> | 250.00<sup>f</sup> |
| B. Propranolol hydrochloride 0.5 mg/kg i.v. | 1.78 | −11.20 | −49.9<sup>f</sup> | −55.00 |
| C. Combination | 3.08 | 1.01 | 28.0 | 49.0 |
| | | Difference Between Post-Drug Phases and Control Na ± % excreted | | |
| A. SK & F 82526-J 10 mg/kg p.o. | 0.82 | −0.32 | −0.08 | −0.175*<sup>f</sup> |
| B. Propranolol hydrochloride 0.5 mg/kg i.v. | 0.59 | 0.12 | 0.31 | 0.75<sup>f</sup> |
| C. Combination | 0.58 | 0.50* | 0.88* | 1.27* |

*Differs significantly from historical control.
<sup>f</sup>Differs significantly from combination.
Four dogs for each determination.

TABLE II

In a similar procedure in four dogs, propranolol in a dose approximately that used intravenously in humans, 20 μg/kg i.v., combined with 10 mg/kg p.o. of 6-chloro-7,8-dihydroxy-1-(p-hydroxyphenyl)-2,3,4,5-tetrahydro-1H-3-benzazepine methylsulfonate (SK&F 82526-J), gave synergistic effects on glomerular filtration rate (GFR) and renal plasma flow (RPF).

| Control Phase I Clearances 1-3 Mean | Phase II Clearances 4-6 | Phase III Clearances 7-9 | Phase IV Clearances 10-12 |
|---|---|---|---|
| | % Changes Post Drug RPF (ml/min) | | |
| 188.13 | 9.48 | 39.35* | 38.42* |
| | | GFR (ml/min) | |
| 50.23 | −4.28 | 8.32* | 19.74* |

*statistically significant

TABLE III

The following data were derived from using a high dose of propranolol, 1 mg/kg, in combination with SK&F 82526-J. With such a high dose of β-blocking agent, the synergistic effects of the combination are less striking because of other compensating cardiovascular action.

| Treatment | Control Phase I Clearances 1-3 Mean | Phase II Clearances 4-6 | Phase III Clearances 7-9 | Phase IV Clearances 10-12 |
|---|---|---|---|---|
| | | % Changes Post Drug RPF (ml/min) | | |
| A. Propranolol hydrochloride 1 mg/kg i.v. | 204.92 | −2.39 | −12.67 | −6.69* |
| B. Combination with SK & F 82526-J 10 mg/kg p.o. | 190.12 | 6.54* | 25.24* | 21.71* |
| | | | GFR (ml/min) | |
| A. Propranolol hydrochloride 1 mg/kg i.v. | 53.69 | 1.49* | 7.87* | 20* |
| B. Combination with SK & F 82526-J 10 mg/kg p.o. | 64.91 | 2.78 | 3.30 | 1.38* |
| | | Difference Between Post-Drug Phases and Control Na ± % excreted | | |
| A. Propranolol hydrochloride 1 mg/kg i.v. | 0.90 | 0.35* | 1.36* | 1.13* |
| B. Combination with SK & F 82526-J 10 mg/kg p.o. | 1.18 | 0.39* | 0.89* | .29* |

*statistically significant

Conclusions

The data in the above tables demonstrate the synergistic renal effects of the β-blocker-renal dopaminergic agent combination on blood flow and sodium ion excretion as well as, especially, on the glomerular filtration rate and the release of renin.

TABLE IV

Comparative Test Data with 7,8-Dihydroxy-1-phenyl-2,3,4,5-tetrahydro-1H-3-benzazepine Hydrobromide, SK&F 38393-C, (U.S. Pat. No. 4,011,319).

Using the same test procedure described above, another dopaminergic benzazepine compound described in the art to have a peripheral or renal mechanism of action, was combined with propranolol hydrochloride to evaluate the renal activity of the combination.

| Treatment | Control Phase I Clearances 1-3 Mean | Phase II Clearances 4-6 | Phase III Clearances 7-9 | Phase IV Clearances 10-12 |
|---|---|---|---|---|
| | | % Changes Post Drug RPF (ml/min) | | |
| A. SK & F 38393-C (20 mg/kg p.o.) (8 dogs) | 216 | 14* | 15* | 20* |
| | | | GFR (ml/min) | |
| | 60 | −* | 2 | 1* |
| | | Difference Between Post-Drug Phases and Control Na ± % excreted | | |
| | 0.89 | 1.34* | 0.91* | .13* |
| | | % Changes Post Drug RPF (ml/min) | | |
| B. SK & F 38393-C (20 mg/kg p.o.) and propranolol hydrochloride (0.5 mg/kg i.v.) | 198.49 | 4.86 | 2.80 | 1.60 |

-continued

| Treatment | Control Phase I Clearances 1-3 Mean | Phase II Clearances 4-6 | Phase III Clearances 7-9 | Phase IV Clearances 10-12 |
|---|---|---|---|---|
| (4 dogs) | | | | |
| | | GFR (ml/min) | | |
| | 57.11 | −0.09 | 2.26 | 4.32* |
| | | Difference Between Post-Drug Phases and Control Na ± % excreted | | |
| | 0.84 | 0.19 | 0.69** | 1.47* |

*Statistically significant $P \leq 0.05$

Conclusions

The data presented in Table IV, when compared with those of Table I, demonstrate (1) no synergistic effect on the renal plasma flow, (2) a slight increase in glomerular filtration rate only in the last collection phase and an (3) increase in natriuresis only in the last two collection phases. This demonstrates the fact that the unexpected biological activity described above can not be demonstrated with all the compounds of the group of dopaminergic benzazepines in the art.

The following examples are designed to teach the preparation and use of the compositions of this invention.

EXAMPLE 1

| Ingredients | Amounts, mg: |
|---|---|
| 6-Chloro-7,8-dihydroxy-1-(4-hydroxyphenyl)-2,3,4,5-tetrahydro-1H—3-benzazepine methylsulfonate as base weight | 100 |
| Propranolol hydrochloride | 40 |
| Sucrose | 25 |
| Calcium sulfate, dihydrate | 50 |
| Talc | 5 |
| Stearic acid | 3 |
| Starch | 10 |

The active ingredients, sucrose, and calcium sulfate are mixed, granulated using hot 10% gelatin solution, meshed and dried. After mixing with the remaining ingredients, the mixture is compressed into a scored tablet.

The scored tablet, per se or broken, is administered orally to a hypertensive patient from 2–4 times daily.

EXAMPLE 2

| FORMULA Ingredients: | mg/cap. |
|---|---|
| 6-Chloro-7,8-dihydroxy-1-(4-hydroxyphenyl)-2,3,4,5-tetrahydro-1H—3-benzazepine methylsulfonate | 131.4* |
| Gelatin | 15.0 |
| Microcrystalline Wax | 5.0 |
| Glyceryl Distearate | 25.0 |
| Non-Pareil Seeds 25/30 Mesh | 123.6 |

*Equivalent to 100 mg free base.

Commercial ethanol, methylene chloride and water are used in the coating operation but are removed during processing.

1. Place the non-pareil seeds in a coating pan.
2. Make an alcoholic gelatin solution (e.g., 10% gelatin in alcohol.
3. Spray the alcoholic gelatin solution onto the pellets until evenly wetted.
4. Disperse 10% of the benzazepine salt evenly on the wetted pellets.
5. Roll pellets in the pan until they are dry enough to repeat the application of gelatin solution and drug powder. Continue coating in this matter until all of the drug powder has been applied. Roll the pellets until dry.
6. Make up a solution of microcrystalline wax and glyceryl distearate in methylene chloride.
7. Coat the stock medicated pellets from Step #5 with the appropriate amounts of wax-fat materials (Step #6) to give the desired release rate characteristics. Roll the pellets until dry.
8. Several such groups of wax-flat pellets from Step #7 are blended with stock medicated pellets to yield the sustained release mix.
9. Add meshed 60 mg of propranolol hydrochloride.
10. Fill into opaque gelatin capsule.

Administer such a capsule orally to a hypertensive patient 1-3 times daily.

EXAMPLE 3

The following compounds (expressed as base weight) are mixed together with 125 g of lactose and 5 mg of magnesium stearate then filled into a hard gelatin capsule. These capsules are administered to a patient in need of improvement in kidney function from 1–4 times daily.

A.     6-Fluoro-7,8-dihydroxy-1-(4-hydroxyphenyl)-2,3,4,5-tetrahydro-1H-3-benzazepine hydrobromide, 75 mg; propranolol hydrochloride, 40 mg.

B.     6-Methyl-7,8-dihydroxy-1-(4-hydroxyphenyl)-2,3,4,5-tetrahydro-1H-3-benzazepine hydrobromide (100 mg), propranolol hydrochloride, 20 mg.

C.     6-Fluoro-7,8-dihydroxy-1-(4-hydroxyphenyl)-2,3,4,5-tetrahydro-1H-3-benzazepine hydrobromide, 125 mg, propranolol hydrochloride, 60 mg.

D.   6-Chloro-7,8-di-isobutyryloxy-1-(4-isobutyryloxyphenyl)-2,3,4,5-tetrahydro-1H-3-benzazepine hydrobromide, 150 mg, propranolol hydrochloride, 40 mg.

E.     6-Chloro-7,8-dihydroxy-1-(4-hydroxyphenyl)-2,3,4,5-tetrahydro-1H-3-benzazepine methane sulfonate-100 mg, metroprolol tartrate, 50 mg.

F.     6-Chloro-7,8-dihydroxy-1-(4-hydroxyphenyl)-2,3,4,5-tetrahydro-1H-3-benzazepine methane sulfonate-100 mg, propranolol hydrochloride-40 mg, hydrochlorothiazide-25 mg.

G.   R-6-Chloro-7,8-dihydroxy-1-(4-hydroxyphenyl)-2,3,4,5-tetrahydro-1H-3-benzazepine methane sulfonate, 75 mg, propranolol hydrochloride-40 mg.

What is claimed is:

1. A composition, in dosage unit form, having activity for improving kidney function comprising:

(A) a nontoxic, renal dopaminergic quantity of a compound of the formula:

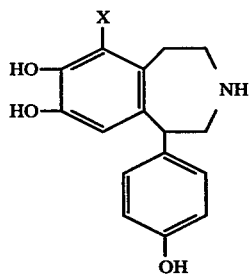

in which X is chloro, fluoro or methyl; one of its pharmaceutically acceptable, acid addition salts, one of its stereoisomers or one of its tri-O-lower alkanoyl esters, each lower alkanoyl group having 2–8 carbon atoms; and (B) a nontoxic, clinically effective quantity of propranolol.

2. The composition of claim 1 in which the quantity of the dopaminergic compound is selected from 15–500 mg.

3. The composition of claim 1 in which the quantity of the dopaminergic compound is selected from 25–300 mg and the quantity of the propranolol is selected from 1–100 mg.

4. The composition of claim 1 in which X is chloro.

5. The composition of claim 1 in which the dopaminergic compound is 6-chloro-7,8-dihydroxy-1-(4-hydroxyphenyl)-2,3,4,5-tetrahydro-1-3H-benzazepine methyl sulfonate and the β-adrenergic blocking compound is propranolol hydrochloride.

6. The composition of claim 5, adapted for oral administration, in which the quantity of dopaminergic compound is selected from the range of 50–150 mg and the quantity of propranolol is selected from the range of 10–80 mg.

7. The method of improving kidney function in a subject in need thereof comprising administering to the subject, orally or parenterally, a dosage unit composition of claim 1.

8. The method of improving kidney function in a subject in need thereof comprising administering to the subject orally a dosage unit of claim 5.

* * * * *